United States Patent [19]

Bicher et al.

[11] 4,332,260

[45] Jun. 1, 1982

[54] EXTERNAL MICROWAVE APPLICATOR AND METHOD

[76] Inventors: James I. Bicher, 2623 Worchester, West Bloomfield, Mich. 48033; Taljit S. Sandhu, 1350 W. Bethune, Apt. 1106, Detroit, Mich. 48202; Fred W. Hetzel, 19324 Addison, Southfield, Mich. 48075

[21] Appl. No.: 160,216

[22] Filed: Jun. 17, 1980

[51] Int. Cl.$^3$ ............................................. A61N 1/40
[52] U.S. Cl. ............................. 128/804; 219/10.55 R
[58] Field of Search ....................... 128/804, 783, 400; 219/10.55 R, 10.55 A

[56] References Cited

U.S. PATENT DOCUMENTS

| | | | |
|---|---|---|---|
| 3,065,752 | 11/1962 | Potzl | 128/804 X |
| 3,307,553 | 3/1967 | Liebner | 128/400 |
| 4,108,147 | 8/1978 | Kantor | 128/804 |
| 4,197,860 | 4/1980 | Sterzer | 128/804 |

FOREIGN PATENT DOCUMENTS 1086062  2/1955  France .................. 128/804

OTHER PUBLICATIONS

Lehmenn et al., "Evaluation of a Microwave Contact Applicator," Arch. Phys. Med. & Rehab., Mar. 1970, pp. 143-146.
Lenox et al., "A Microwave Applicator . . .", IEEE Trans. on Microwave Theory & Techniques, vol. 24, No. 1, pp. 58-61, Jan. 1976.
Guy et al., "Development of a 915-Megahertz Direct-Contact Applicator for Therapeutic Heating of Tissues IEE Trans Microwave Theory Tech.", 26(8): 550-556, (1978), (abstract).
Cheung et al., "Dual-Beam TEM Applicator for Direct-Contact Heating of Dielectrically Encapsulated Malignant Mouse Tumor", Radio Science, vol. 12, No. 6, Supp. Nov.-Dec., 1977, pp. 81-85.
Sandhu et al., "Applicator Design and Microwave Frequency Selection for Localized Hyperthermia Equipment Suitable for Clinical Treatment: Proceedings of a Conference on Clinical Prospects for Hypoxic Cell Sensitizers and Hyperthermia," Madison, WI, Sep. 30 to Oct. 2, 1977, p. 36, 1978.
Hahn, G. M., "Radio Frequency, Microwaves and Ultrasound in the Treatment of Cancer: Some Heat Transfer Problems", p. 22, Conference on Thermocharacteristics of Tumors: Applications and Detection and Treatment, N.Y., N.Y., 14-16, Mar. 1979, New York Academy of Sciences, N.Y., N.Y., 1979.
Atkinson, "Assessment of Current Hyperthermia Technology", Cancer Research; 39 (6), part 2, pp. 2313-2324, (1979).
Kowal et al., "Applicator Design and Microwave Frequency Selection for Local Hyperthermia/Whole--Body Hyperthermia Equipment Suitable For Clinical Treatment", Am. J. Roentgenol. Radium Therm. Nucl. Med.: 130(1): 188, (1978).

Primary Examiner—Lee S. Cohen
Attorney, Agent, or Firm—Garrettson Ellis

[57] ABSTRACT

The skin surface of a patient may be irradiated with the microwaves of a frequency of 250 to 353 MHz (i.e., a wavelength of about 85 to 120 cm.). A conductive metal housing having an open bottom and closed walls on all other sides overlies the skin surface. The interior of the housing carries a pair of opposed slabs of material having a dielectric constant of more than 4 and defining a space therebetween. The microwaves are radiated from a microwave antenna projecting into said space through a wall in the housing, with the antenna being generally parallel to the open bottom. The slabs are of sufficient thickness to provide generally uniform electric and magnetic field intensities throughout the space. During operation, air is blown into the space through an aperture in a wall of the housing to cool the skin with the air passing out of the open bottom.

11 Claims, 2 Drawing Figures

EXTERNAL MICROWAVE APPLICATOR AND METHOD

BACKGROUND OF THE INVENTION

The microwave treatment of cancer is a growing clinical alternative to X-ray treatment and chemotherapy. Basically, the microwaves heat the tissue. Malignant tumors have been found to be often more sensitive to heat than normal tissues, so the careful application of microwaves can destroy the malignant tumors while the normal tissue survives.

In Kantor U.S. Pat. No. 4,108,147, a microwave applicator is disclosed. It comprises an open-bottom container having a pair of opposed Teflon slabs spaced from each other. The microwaves are propagated in the space between the slabs for treatment of skin exposed to the open bottom of the applicator.

Various disadvantages of this design of applicator exist. First, the applicator is designed for use with diathermy radiation of about 2.45 GHz. A disadvantage of this is that such radiation only penetrates a relatively small distance into the tissue, typically less than 2 cm. Furthermore, superficial burns on the skin are a continuous problem with a structure like this, since the microwave absorption is concentrated near the skin surface.

Also, microwave applicators have been utilized at 915 MHz among other frequencies, but with apparent effective penetration of only 1 or 2 cm. into the muscle because of the inherent lack of penetration capability of microwaves at that frequency (Lehmann et al: *Evaluation of a Therapeutic Direct-Contact 915-MHz Microwave Applicator for Effective Deep-Tissue Heating in Humans.* IIEE Trans Microwave Theory Tech; 26(8): 556–563 (1978).

In accordance with this invention, a microwave applicator is provided for irradiating the skin surface of a patient, but with substantially increased effective penetration of 5 to 6 cm. At the same time, the danger of skin burns can be greatly reduced with the method and apparatus of this invention, with the apparatus being inexpensive and compact for ease of clinical use.

DESCRIPTION OF THE INVENTION

In accordance with this invention, the skin surface of a patient may be irradiated with microwaves of a frequency of 250 to 353 MHz (which is equivalent to a wavelength of about 85 to 120 cm.). Preferably from 270 to 330 MHz may be used.

A conductive metal housing is overlaid in spaced relation over the skin surface to be treated. The conductive metal housing has an open bottom and closed walls on all other sides, with the interior of the housing carrying a pair of opposed slabs of material having a dielectric constant of more than 4 and preferably about 6, and defining a space therebetween.

Microwaves are radiated from a microwave antenna projecting through a wall of the housing into the space, the antenna being in generally parallel relation to the open mouth.

The slabs are of sufficient thickness to provide generally uniform electric and magnetic field intensities throughout the space.

Simultaneously, air is blown into the space through an aperture in a wall of the housing to cool the skin, as the air passes out of the open mouth and across the skin.

It has been found that the microwave frequency of 270 to 330 MHz provides unique advantages for microwave treatment, particularly because of the increased capability of microwave radiation of this frequency to effectively penetrate tissue to approximately 5 or 6 cm. Accordingly, a large area of the lung, for example, can be irradiated with the apparatus of this invention for the treatment of lung cancer, even though the microwave applicator device remains out of direct contact with the body.

In the prior art it would have often been impracticable to utilize microwaves at this frequency. For example, referring to the previously cited U.S. Pat. No. 4,108,147, a uniform field could not realistically be provided to microwaves of the frequency of this invention with the Teflon slabs utilized therein, without the Teflon slabs being impracticably thick so as to create problems of bulk, expense, and weight. Accordingly, the opposed slabs of dielectric material utilized in this invention have a dielectric constant of more than 4 to reduce its necessary thickness to provide a uniformly propagated field in the space between the respective slabs. Preferably, the dielectric constant of the slabs are 6 or more, and the slabs are made of a cellular material such as a foam for a very substantial weight reduction.

It is also desirable for the aperture through which air is blown to contain screening of conductive metal wire. The effect of this is to essentially eliminate microwave leakage through the aperture.

Accordingly, the microwave applicator of this invention may be compact and lightweight, yet at the same time providing microwaves of a frequency of 270 to 330 MHz for deep penetration into tissues. Simultaneously, the air inlet system provides a constant stream of air across the irradiated skin, tending to reduce the danger of burning of the skin during microwave treatment.

Preferably, the opposed slabs of dielectric material described above have a thickness s, with the dielectric constant E being more than 4, as stated above. With the wavelength λ of the radiation used herein being preferably 90 to 110 cm., the relationship of the specific values for λ, s, and E are preferably essentially:

$$s\sqrt{E-1} = \lambda/4$$

Furthermore, the distance between the slabs is preferably not more than $$\frac{\lambda}{\pi} \cot^{-1}\left[\tan\left(\frac{\pi}{2}\sqrt{E/E-1}\right)\right]$$

so that a uniform microwave field can be propagated throughout the entire space between the slabs.

It is also preferable for the width of the slabs to be no more than one-half of the specific wavelength of microwaves used.

Antenna aperture means are also preferably provided to permit insertion of the microwave antenna into a space in a position generally parallel to the open bottom. Typically the antenna aperture is defined in a side wall that is not associated with one of the dielectric slabs.

DESCRIPTION OF DRAWINGS

Referring to the drawings.

DESCRIPTION OF SPECIFIC EMBODIMENT

Figure 1:
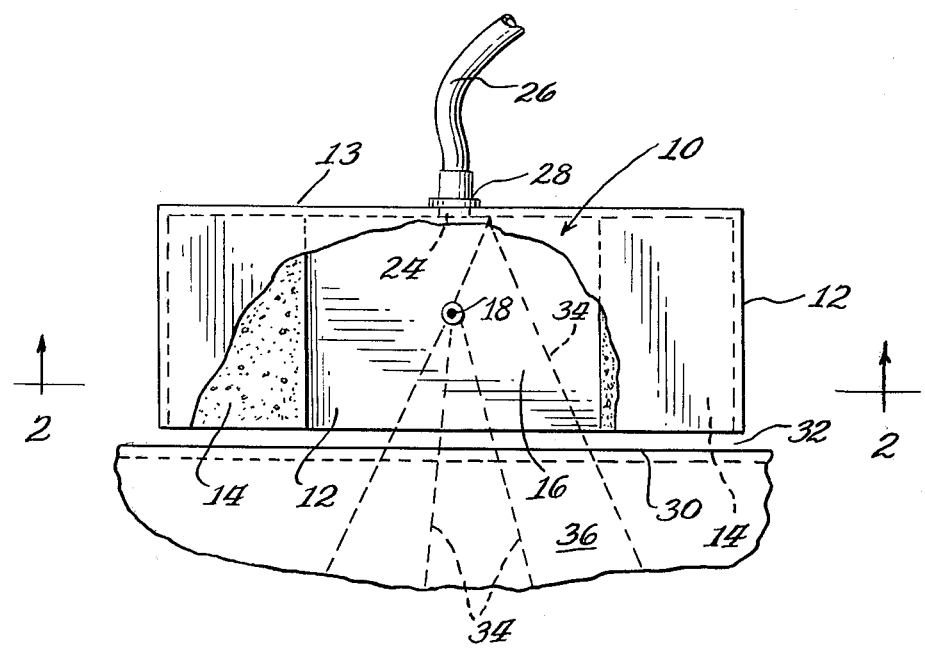
FIG. 1 is an elevational view, with portions broken away, of the external microwave applicator or waveguide of this invention.
Figure 2:
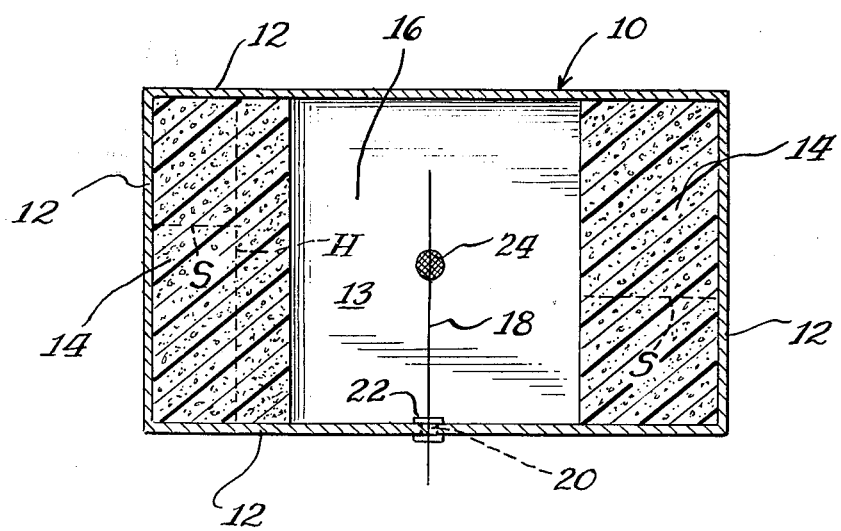
FIG. 2 is a sectional view taken along line 2—2 of FIG. 1.

Referring to the drawings, the microwave applicator waveguide of this invention comprises a conductive metal, hollow, rectangular housing 10 defining side walls 12 and an open bottom, as shown.

In the interior of housing 10, opposed slabs of dielectric material 14 are provided, preferably having a thickness governed by the equation recited above.

The material of slabs 14 may be a dielectric foam having a dielectric constant of 6, sold under the trademark ECOFOAM by Emerson & Cumings, Inc. of Canton, Mass.

This lightweight, flexible material provides the desired dielectric characteristics so that a uniform microwave field may be produced without the use of ungainly and excessive thicknesses of dielectric materials.

Alternatively, other materials such as ceramic blocks and especially ceramic foams having the requisite dielectric constant may be utilized for slabs 14, if desired.

As shown, slabs 14 of dielectric material define a space 16, in which space a generally uniform field of microwaves may be propagated. Specifically, slabs 14 may be 11.2 cm. thick, for a wavelength of 102 cm.

Microwave antenna 18, of any known and desired design, passes through aperture 20 in one of the side walls 12, being retained by a dielectric sleeve 22.

Aperture 24 in top wall 13 is provided, being preferably occluded by a copper wire screening or mesh of sufficiently small aperture size so that microwaves are not propagated through the aperture in any significant quantities.

Air hose 26 may be attached to nut 28, or with any other retention structure as desired, so that cold air may pass into space 16.

In operation, microwave applicator or waveguide 10 is brought into close proximity with the skin 30 of a patient, leaving a small rectangular gap 32 of 1 cm. or the like between the patient's skin 30 and waveguide 10. Microwaves, preferably of a wavelength of essentially 100 cm., are propagated from antenna 18 with the configuration of waveguide 10 being proportioned in accordance with the equations described above to cause the generation of an essentially uniform microwave field throughout space 16. Microwaves 34 as shown in FIG. 1 are propagated in their uniform field, being modulated by dielectric slabs 14 and reflected by the walls 12, 13 of housing 10, to penetrate approximately 5 or 6 cm. through the skin 30 and into the underlying tissue 36 of the patient. Thus, deep tumors may be irradiated from the skin surface of the patient, utilizing the preferred wavelength and frequency of microwaves, with the structure of waveguide as disclosed herein.

Simultaneously, cooling air passes through aperture 24 into space 16, from there passing in a stream along the skin 30 and out gap 32, thus removing heat from the skin during the microwave irradiation operation. The amount of cooling can, of course, be adjusted by the amount of air passing into the space 16 through aperture 24.

By way of example, the distance between slabs 14 may be about 20 cm. if desired while the width H of slabs 14 may be 20 cm. If desired, these latter two dimensions may be adjusted over a substantial range to control the area of the patient which is irradiated, so that the applicator of this invention may be used by appropriate assembly and adjustment, to provide irradiation to the exact area dictated by the specific therapeutic need of the patient.

The above has been offered for illustrative purposes only, and is not intended to limit the invention of this application, which is as defined in the claims below.

We claim:

1. The method of irradiating the skin surface of a patient with microwaves of a frequency of 250 to 353 MHz for treating tumors, which comprises:

overlaying, in spaced relation, the skin surface to be treated with a conductive metal housing having an open bottom overlaying said skin and having closed walls on all other sides, the interior of said housing carrying a pair of opposed slabs of dielectric material having a dielectric constant of more than 4 and defining a space therebetween;

radiating microwaves of said frequency from a microwave antenna projecting through a wall of said housing into said space, said antenna being generally parallel to said open bottom, said slabs being of sufficient thickness to provide generally uniform electric and magnetic field intensities throughout said space; and simultaneously blowing air into said space through an aperture in a wall of said housing to cool the skin.

2. The method of claim 1 in which said aperture contains screening of conductive metal wire to essentially eliminate microwave leakage therethrough.

3. The method of claim 2 in which said aperture is positioned in the top wall of said housing.

4. A waveguide for controlling and rendering generally uniform a microwave field of a wavelength λ of 85 to 120 cm. for direct skin application tumor therapy, said waveguide comprising a conductive metal housing having an open bottom and having closed walls on all other sides, the interior of said housing carrying a pair of opposed slabs of dielectric material having a thickness s, a dielectric constant E of more than 4, and defining a space therebetween, the relationship of the specific values for λ, s, and E being essentially:

$$s\sqrt{E-1} = \lambda/4$$

the distance between said slabs being no more than $$\frac{\lambda}{\pi} \cot^{-1}\left[\tan\left(\frac{\pi}{2}\sqrt{E/E-1}\right)\right];$$

and the width of said slabs being no more than one-half of the specific wavelength used;

blow aperture means in a wall of said housing to permit the blowing of air into said space, and antenna aperture means in a wall thereof to permit insertion of a microwave antenna into said space in a position generally parallel to said open bottom.

5. The waveguide of claim 4 in which said housing defines a rectangular box.

6. The waveguide of claim 4 in which said blow aperture means is covered with conductive metal screening to essentially eliminate microwave leakage through said blow aperture means.

7. The waveguide of claim 4 in which E is at least 6, and said slabs are made of a cellular material.

8. The waveguide of claim 4 in which said wavelength is essentially 100 cm.

9. A waveguide for controlling and rendering generally uniform a microwave field of a wave length λ of 85 to 120 cm. for direct skin application tumor therapy, said waveguide comprising a conductive metal housing having an open bottom and having closed walls on all other sides, the interior of said housing carrying a pair of opposed slabs of cellular material having a thickness s, a dielectric constant E of more than 4, and defining a space therebetween, said conductive metal housing defining a rectangular box, the relationship of the specific values for λ, s, and E being essentially:

$$s\sqrt{E-1}=\lambda/4$$

the distance between said slabs being no more than $$\frac{\lambda}{\pi}\cot^{-1}\left[\tan\left(\frac{\pi}{2}\sqrt{E/E-1}\right)\right]$$

and the width of said slabs being no more than one-half of the specific wavelength used;

blow aperture means in a wall of said housing to permit the blowing of air into said space to cool the skin during operation, said blow aperture means being covered with conductive metal screening to essentially eliminate microwave leakage through said blow aperture means, and antenna aperture means in a wall of said housing to permit insertion of a microwave antenna into said space in a position generally parallel to said open bottom.

10. The waveguide of claim 9 in which E is 6.0, s is 11.2 cm., and λ is 102 cm.

11. The waveguide of claim 9 in which said slabs of material comprise a foamed plastic material having a dielectric constant of at least about 6.

* * * * *